United States Patent [19]

Le Clair et al.

[11] 4,371,390

[45] Feb. 1, 1983

[54] FLOWABLE HERBICIDES

[75] Inventors: Francis J. Le Clair, Webster Groves; John M. Surgant, Clayton, both of Mo.

[73] Assignee: Monsanto Company, St. Louis, Mo.

[21] Appl. No.: 210,717

[22] Filed: Nov. 26, 1980

Related U.S. Application Data

[63] Continuation of Ser. No. 957,125, Nov. 3, 1978, abandoned.

[51] Int. Cl.³ .................. A01N 25/02; A01N 25/00
[52] U.S. Cl. ................................. 71/93; 71/118; 71/DIG. 1
[58] Field of Search .............. 71/DIG. 1, 118, 93

[56] References Cited

U.S. PATENT DOCUMENTS

| | | | |
|---|---|---|---|
| 2,863,752 | 12/1958 | Hamm et al. | 71/118 |
| 2,891,855 | 6/1959 | Gysin et al. | 71/74 |
| 2,909,420 | 10/1959 | Gysin et al. | 71/74 |
| 3,442,945 | 5/1969 | Olin | 260/562 |
| 3,547,620 | 12/1970 | Olin | 71/118 |
| 3,948,636 | 4/1976 | Marks | 71/112 |

FOREIGN PATENT DOCUMENTS

| | | |
|---|---|---|
| 751164 | 11/1970 | Belgium . |
| 630606 | 11/1961 | Canada . |
| 167029 | 6/1976 | Hungary . |
| 1302720 | 1/1973 | United Kingdom . |
| 1421092 | 1/1976 | United Kingdom . |
| 1554595 | 10/1979 | United Kingdom . |

*Primary Examiner*—Catherine L. Mills
*Attorney, Agent, or Firm*—Patricia A. Coburn; Howard C. Stanley

[57] ABSTRACT

The disclosure herein pertains to the field of flowable herbicides and process and materials for their preparation. In particular, flowable 2-haloacetanilides, e.g., propachlor and mixtures of 2-haloacetanilides with triazines, e.g., atrazine are disclosed.

6 Claims, No Drawings

FLOWABLE HERBICIDES

This is a continuation of application Ser. No. 957,125 filed Nov. 3, 1978, now abandoned.

BACKGROUND OF THE INVENTION

1. Field of the Invention

The invention herein pertains to the field of flowable herbicides, materials and processes for preparation thereof. In particular, flowable herbicides comprising acetanilides, e.g., propachlor, and mixtures thereof with triazines, e.g., atrazine, and appropriate emulsifying-/suspending agents, solvents and carriers are disclosed.

2. Description of the Prior Art

The prior art with respect to herbicides comprises wettable powders (WP's) emulsifiable concentrates (E.C.'s), granules and flowable formulations which may be prepared as package mixes or tank mixes.

As relevant to the present invention which pertains to flowable herbicides comprising certain 2-haloacetanilides alone or in combination with certain s-triazines, the prior art describes a variety of formulations in the above forms. For example, U.S. Pat. No. Re. 26,961 (original U.S. Pat. No. 2,863,752) and U.S. Pat. Nos. 3,442,945 and 3,547,620 describe various 2-haloacetanilides, e.g., propachlor, alachlor, butachlor, etc., which may be used alone or in admixture with herbicides including various triazines, including s-triazines. U.S. Pat. Nos. 2,891,855 and 2,909,420 describe various triazines, e.g., atrazine, and Canadian Pat. No. 847,250 refers to the combination of certain s-triazines with alachlor in various forms, e.g., solutions, emulsions, suspensions, or dusts. However, this patent does not give any details as to the materials (except active ingredients) or processes for producing any of these forms of formulations.

In addition to the above patent literature, there are commercial formulations of flowable propachlor and flowable atrazine which are applied as tank mixes.

The above prior art, the most relevant known to the inventors, is devoid of any disclosure or other description of a unitary flowable herbicide comprising a 2-haloacetanilide, e.g., propachlor or alachlor, and an s-triazine, e.g., atrazine. The commercial flowable propachlor and flowable atrazine mentioned above are each of proprietary composition, hence, unknown to the inventors. In addition, these flowable herbicides must be prepared separately, packaged separately, transported and stored in separate containers and used as a tank mix. As will be shown below, the flowable propachlor of this invention has superior properties as an independent flowable herbicide, i.e., having only one active ingredient, vis-a-vis said commercial flowable propachlor.

Problems associated with prior art forms of acetanilide and/or s-triazine formulations include the need to convert wettable powder forms of these solid materials into slurries to be used by the farmer in preparing tank mixes for application to the soil. The preparation of slurries of wettable powders of some herbicides, e.g., of prominent note is propachlor, presents certain safety hazards and inconveniences due to the generation of noxious dusts which are irritable to the skin and hazardous to breathe. In addition, wettable powders of propachlor and atrazine when prepared as tank mixes do not disperse well, have poorer spontaneity of "bloom", have lower suspensibility, poor redispersibility and poorer compatibility with liquid fertilizers than do liquid formulations such as emulsifiable concentrates and flowable formulations.

Water-based flowable herbicides have advantages over emulsifiable concentrates since the latter generally required organic solvents which are usually flammable and/or of toxic composition, hazardous to the skin or from vapors evolved therefrom. Flowable herbicides do not suffer the usual disadvantages of wettable powders, dusts and emulsifiable concentrates mentioned above, are easier to prepare and use and have the same, and sometimes superior, herbicidal efficacy and crop safety as older forms of formulation mentioned above. Moreover, flowable herbicides generally, and in the present invention specifically, have superior properties with respect to suspensibility, viscosity, bloom, redispersibility, stability (e.g., shelf-life and temperature cycling) and compatibility with liquid fertilizers.

It is a particular advantage of the present invention to provide a combination flowable herbicide comprising a 2-haloacetanilide and an s-triazine, e.g., flowable propachlor and atrazine, which may be prepared, transported, stored and used as a one-container herbicide having none of the disadvantages of prior art herbicides and all of the advantages mentioned hereinabove.

As used herein and in the art a "flowable herbicide" denotes a suspension of solid particles in a liquid carrier.

SUMMARY OF THE INVENTION

This invention relates to flowable herbicides comprising certain 2-haloacetanilides as the sole active ingredient or in combination with certain s-triazines and to a process for preparing these herbicides.

In more particular, this invention pertains to flowable herbicides having the following composition by weight:

(a) from 25% to 50% of a 2-haloacetanilide having the formula

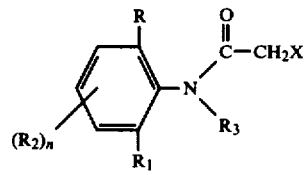

wherein
R, $R_1$ and $R_2$ are hydrogen $C_{1-6}$ alkyl, alkoxy or alkoxyalkyl groups,
$R_3$ is hydrogen, $C_{1-8}$ alkyl, alkenyl, akynyl or alkoxy radicals,
X is chloro, bromo or iodo and
n is an integer from 0–3 inclusive;

(b) from 0 to 15% of an s-triazine having the formula

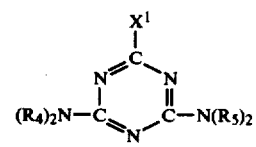

wherein
$X^1$ is chloro, bromo or iodo,
$R_4$ and $R_5$ are independently hydrogen or $C_{1-5}$ alkyl, alkenyl, hydroxyalkyl, arylalkyl or cycloalkyl;

(c) an emulsifier/suspension system for components (a) and (b) comprising (i) hydrated amorphous silicon dioxide: 2–8%
(ii) polyoxypropylene/polyoxyethylene block copolymer: 2–8%
(iii) lower alkyl-substituted $C_{8-10}$ alkyne diol or ethyl ester thereof and: 0–2%
(iv) hydrated aluminum silicate: 0.5–2%
(d) an inert, low-freezing point solvent compatible with components (c) (i)–(iv): 5–15%
(e) defoamer: 0–0.1%, and
(f) an inert liquid carrier for components (a)–(e): 30–70%
the solid components of said composition having a particle size no greater than 25 microns.

In preferred embodiments of this invention, the flowable herbicide comprises propachlor, i.e., 2-chloro-N-isopropyl acetanilide, as the sole active ingredient or in combination with atrazine, i.e., 2-chloro-4-(ethylamino)-6-isopropylamino-s-triazine. When used alone, propachlor is present in a preferred concentration of from about 35–48% by weight of the flowable herbicide, and in more preferred embodiments from 40–46%, whereas in combination with atrazine, the concentration of propachlor is reduced generally by the amount of added atrazine, which preferably is present in an amount of from 5–15% and more preferably within the range of about 10–15%, the amount of active ingredients depending upon the particular weed spectrum to be treated.

The active ingredients in the flowable herbicides of this invention are maintained in an emulsification/suspension system comprising a unique and critical combination of (1) hydrated amorphous silicas exemplified by products similar to trade-named Hi-Sil, e.g., Hi-Sil 233 or Zeofree 80; (2) aqueous alcoholic solutions of polyoxypropylene/polyoxyethylene (P.O.P.-P.O.E.) block copolymers, trade-named Pluraflo, e.g., Pluraflo E4 and E5, having molecular weights on the order of 6500; (3) lower alkyl-substituted alkyne diols, (tradename Surfynol) exemplified by dimethyl octynediol (Surfynol 82), tetramethyl decynediol (Surfynol 104) and the ethoxylated esters thereof, e.g., Surfynol 465 and Surfynol 485 (10 moles and 30 moles respectively of ethoxylated Surfynol 104) and (4) a hydrated aluminum silica, such as kaolin and the like. An inert, low-freezing point solvent, e.g., polyglycols, which are compatible with said emulsfication/suspension system and with water is also used. Preferably, a defoamer such as a 10% solution of Corak 100, a non-aqueous silicone antifoam compound having 100% silicone solids, is used, but is not critical and, finally, the balance of the flowable composition is made up with water.

The novel flowable herbicides of this invention were only made possible by discovery and development of a novel process. In particular, the process of this invention involves mixing the relevant components in appropriate quantities in a pre-grind operation in order to blend the ingredients and obtain a suitable solids particle size distribution and facilitate the final wet grinding operation. A preferred particle size distribution is as follows: 95% less than 48 microns; 75% less than 35.5 microns; 50% less than 23 microns; and 25% less than 13 microns. The final grinding operation may be conducted in vertical or horizontal media mills using stainless steel, ceramic or other ball grinding materials which are inert with respect to the reaction components. Critical parameters in the final wet-grind operation are that the temperature be maintained below about 20° C. and the grinding or milling operation continued until the solids particle size distribution is as follows: 95% less than 20 microns; 75% less than 10 microns; 50% less than 5 microns and 25% less than 2.5 microns. In preferred flowable herbicide embodiments the solids particle-size distribution is as follows: 95% less than 4.5 microns; 75% less than 2.8 microns, 50% less than 2.4 microns and 25% less than 1.9 microns.

Preferred 2-haloacetanilides according to the above formula are solids. When liquid 2-haloacetanilides are used, it is unnecessary to use the clay (kaolin) and hydrated silicon dioxide (Hi-Sil 233) components in the emulsification/suspension system, other surfactants and gels may be used to suspend the liquid active ingredient. Of primary interest and preference herein is the use of propachlor either alone or in combination with an s-triazine. Other preferred 2-haloacetanilides according to the above structural formula include those wherein the R members are independently hydrogen, $C_{1-5}$ lower alkyl or alkoxy groups; exemplary of such compounds, e.g., alachlor, etc., are enumerated in the above-mentioned U.S. Pat. Nos. 3,442,945 and 3,547,620.

Preferred s-triazines are those according to the above formula wherein the $R_4$ and $R_5$ members are hydrogen and $C_{1-4}$ lower alkyl. In particular, the triazine of primary interest is atrazine and related compounds within the above formula, esp. simazine, i.e., 2-chloro-4,6-bis(ethylamino)-s-triazine, and propazine, i.e., 2-chloro-4,6-bis(isopropylamino)-s-triazine, and the like.

DETAILED DESCRIPTION OF THE INVENTION

EXAMPLE 1

This example describes a preferred embodiment of the invention for preparing a flowable herbicide containing propachlor as the active ingredient.

The following components were fed to a mixer for a pre-grind mixing and blending operation in the indicated proportions:

| Component | Lb/Gal | (Kg/L) | 5 Gal | (L) | Percent By Weight |
|---|---|---|---|---|---|
| Propachlor (95)% | 4.260 | (0.51) | 21.30 | (80.62) | 44.8 |
| Hi-Sil 233 | 0.380 | (0.05) | 1.90 | (7.19) | 4.0 |
| Kaolin (Barden Clay) | 0.100 | (0.01) | 0.50 | (1.89) | 1.0 |
| Pluraflo 5E | 0.380 | (0.05) | 1.90 | (7.19) | 4.0 |
| Ethylene glycol | 0.748 | (0.09) | 3.74 | (14.16) | 8.0 |
| Corak 100 | 0.002 | (0.0002) | 0.01 | (0.04) | 0.02 |
| Water | 3.620 | (0.43) | 18.10 | (68.51) | 38.18 |
| | 9.500 | (1.14) | 47.45 | (179.60) | 100.00 |

The above formulation was ground in one gallon increments for 10 minutes for each gallon while maintaining the temperature at less than about 25° C., preferably about 20° C., until the solids were reduced to a particle size corresponding to the following distribution: 95% less than 48 microns; 75% less than 35.5 microns; 50% less than 23 microns and 25% less than 13 microns. The mixture is sampled for assay; any necessary adjustments are made based on the sample analysis.

The pre-ground mixture is then pumped to a surge tank, thence fed to a horizontal media mill, e.g., a Dyno-Mill, at a throughput volume of 7 liters/hour, while maintaining the temperature at about 18°–20° C. Solids in the formulation leaving the media mill had a particle size distribution as follows: 95% less than 4.5 microns; 75% less than 2.8 microns; 50% less than 2.4 microns and 25% less than 1.9 microns.

EXAMPLE 2

Following the same procedures described in Example 1, but adding atrazine containing small amounts, e.g., from 0.5–5.0%, of atrazine-related compounds, i.e., homologs such as propazine and simazine, the following flowable formulation was prepared:

| Component | Lb/Gal | (Kg/L) | 5 Gal | (L) | Percent By Weight |
|---|---|---|---|---|---|
| Propachlor (95%) | 3.20 | (0.38) | 16.00 | (60.56) | 33.605 |
| Atrazine (97%) | 1.06 | (0.13) | 5.30 | (20.06) | 11.195 |
| Hi-Sil 233 | .38 | (0.05) | 1.90 | (7.19) | 4.00 |
| Kaolin | .10 | (0.01) | 0.50 | (1.89) | 1.00 |
| Plurflo 5E | .38 | (0.05) | 1.90 | (7.19) | 4.00 |
| Ethylene glycol | .75 | (0.09) | 3.74 | (14.16) | 8.00 |
| Corak 100 | .002 | (0.0002) | 0.01 | (0.04) | 0.02 |
| Water | 3.620 | (0.43) | 18.10 | (68.51) | 38.18 |
|  | 9.50 | (1.14) | 47.45 | (179.60) | 100.00 |

The solids particle sizing of this formulation had the same distribution as in Example 1.

Similar flowable formulations as the above having varying amounts of active ingredients have also been prepared in vertical media mills, called attritors. In any case, the essential criteria are that the process cooling temperatures be maintained at or below about 20° C., formulation assay be maintained at the correct composition and that the solids particle size be maintained below about 48–50 microns in the pre-mix and below 25 microns, preferably below 20 microns and still more preferably below 5 microns, i.e., according to the size distribution shown in Example 1.

EXAMPLE 3

In order to illustrate the relative performance and superior physical properties of the flowable herbicides of this invention vis-a-vis the most closely-related herbicides of the prior art, tests were conducted to determine the relative "bloom" and redispersability of these formulations; the results of these tests are tabulated in Table 1 below.

The test procedures are as follows: a weighed amount of the herbicidal formulation (20 grams) is poured into a 250 ml glass stoppered graduate containing 230 cc of standard hard water through a 6 ml glass powder funnel. The degree of spontaneous emulsification ("bloom") is observed. The criteria for judging bloom is as follows: "Perfect"—a thick emulsion cloud descending to the bottom of the graduate without separation of any type; "Good"—thin bloom with no separation or thick bloom with minor separation such as "emulsion trailing" at 2" or less from the bottom of the graduate and "Poor"—an emulsion cloud containing droplets breaking from the emulsion at the half-way point between the surface and bottom of the graduate; no oil droplets throughout bloom at 1" from bottom of graduate.

The property of "redispersability" is determined by inverting the stoppered graduated cylinder until all separated material is resuspended; observations are made typically after 0.5, 1.0 and 24 hours. The number of inversions required for complete redispersion is a measure of the degree of redispersability of the herbicidal formulation. In Table 1, the numbers under the "Redispersability" column refer to the number of inversions required to effect resuspension of the respective herbicide formulations. The letter symbols under the "Formulation" column refer to formulations identified as follows:

A. Flowable propachlor according to this invention containing 4 lb/gal (0.48/kg/l) of propachlor;

B. Flowable propachlor commercially available under the trade name "Bexton 4L" also containing 4 lb/gal of propachlor.

C. Flowable propachlor/atrazine according to this invention containing 3.0 lb/gal (0.36 kg/l) propachlor and 1 lb/gal (0.120 kg/l) of atrazine and related atrazine compounds.

D. Bexton 4L flowable propachlor tank-mixed with flowable atrazine commercially available under trade name "Aatrex 4L" in proportions of 3:1 propachlor:atrazine [in lbs/gal (kg/l)].

E. Bexton 4L flowable propachlor tank-mixed with flowable atrazine commercially available under trade name "Co-Op 4L" in proportions of 3:1 propachlor:atrazine [in lbs/gal. (kg/l)].

TABLE 1

| Formulation | Bloom | Property Redispersability | | |
|---|---|---|---|---|
|  |  | 0.5 Hr. | 1.0 Hr. | 24 Hrs. |
| A | Perfect | 2 | 2 | 3 |
| B | Poor | 2 | 6 | 11 |
| C | Perfect | 1 | 2 | 2 |
| D | Good | 6 | 12 | 30 |
| E | Good | 5 | 10 | 30 |

Reference to the data in Table 1 demonstrates that Formulations A and C, i.e., flowable formulations according to this invention, are superior to analogous formulations of the prior art in the important properties of bloom and redispersability. The ability of a herbicide to readily redisperse after 24 hours is an important feature to a farmer who for one reason or another, e.g., rain, must delay applying a tank mix of the herbicide for a day or so.

It has been found that tested flowable herbicidal formulations of this invention display excellent suspensibility and redispersability in high salt solutions such as nitrogen or other fertilizer solutions when used as a tank mix. For example, Formulations A and C in Table I were found to be compatible in a fertilizer solution comprising ammonium nitrate (38.8%), urea (31.0%) and water (30.2%). On the other hand, these formulations, (as well as the other formulations in Table 1), displayed flocculation when tested in high-phosphorus fertilizer solutions having nitrogen:phosphorus:potassium ratios of 1:3:1.

The flowable herbicide formulations of this invention have particular utility in corn and sorghum in which the crop safety and herbicidal efficacy are equivalent to wettable powder tank mixes currently in use. In comprehensive field tests comparing preferred propachlor and propachlor/atrazine flowable formulations with wettable formulations it has been found that there are no significant differences in weed control, crop safety or yield between these herbicide formulations. Typical of such field tests are illustrated in the following examples.

EXAMPLE 4

A flowable propachlor/atrazine formulation corresponding to that described in Example 2 and a comparable wettable powder (WP) propachlor/atrazine tank mix were tested in sorghum against redroot pigweed (RPW), puncture vine (PV), crabgrass (CG) and barnyardgrsss (BYG). The respective herbicide formulations were applied pre-emergence at 3.32 lb/A (3.72 kg/Ha) for the flowable and 3.34 lb/A (3.81 kg/Ha) for the wettable powder on sandy loam soil. Observations were taken at 28 days and 58 days after treatment (DAT) and the following results noted (expressed in terms of percent injury to the indicated plants):

| Formulation | Percent Injury | | | | | |
| --- | --- | --- | --- | --- | --- | --- |
| | Sorghum, | RPW, | PV, | CG, | BYG | DAT |
| Flowable propachlor/atrazine | 4 | 78 | 62 | 92 | 92 | 28 |
| | 0 | 75 | 72 | 82 | 85 | 58 |
| WP propachlor/atrazine | 4 | 78 | 62 | 92 | 92 | 28 |
| | 0 | 80 | 83 | 80 | 83 | 58 |

EXAMPLE 5

This example illustrates tests with flowable propachlor/atrazine according to Example 2 and a comparable tank mix of wettable powder propachlor/atrazine in corn against various grasses and lambsquarter (LBQ). The respective formulations were applied preemergence at 4.3 lb/A (4.82 kg/Ha) for the wettable powder and 4.0 lb/A (4.48 kg/Ha) for the flowable formulation. Observations were made 42 days after treatment with the following results:

| Formulation | Percent Injury | | |
| --- | --- | --- | --- |
| | Corn | Grasses | LBQ |
| flowable propachlor/atrazine | 0 | 41 | 65 |
| WP propachlor/atrazine | 0 | 60 | 86 |

EXAMPLE 6

A flowable propachlor formulation corresponding to that described in Example 1 and a comparable wettable powder propachlor tank mix were tested in corn against redroot pigweed (RPW), lambsquarter (LBQ), blacknightshade (BNS) and green foxtail (GRFT). The respective herbicide formulations were applied at a rate of 4 lb/A (4.48 kg/Ha) of active ingredient by preplant incorporation into soil of loamy sand composition containing 1.2% organic matter. Observations were made 28 days after treatment. There was only a slight (3%) injury to the corn with both formulations and herbicidal efficacy compared as follows (in terms of percent injury):

| | RPW | LBQ | BNS | GRFT |
| --- | --- | --- | --- | --- |
| Wettable Powder propachlor | 100 | 100 | 90 | 97 |
| Flowable propachlor | 100 | 74 | 84 | 57 |

EXAMPLE 7

A flowable propachlor formulation corresponding to that described in Example 1 and a comparable wettable powder (WP) propachlor tank mix were tested in sorghum against red-root pigweed (RPW), green foxtail (GRFT), witchgrass (WTG) and barnyardgrass (BYG). The respective herbicide formulations were applied pre-emergence at 4.0 lb/A (4.48 kg/Ha) on silt loam soil having 1.5% organic matter. Observations were taken at 30 days and 78 days after treatment (DAT) and the following results noted, expressed in terms of percent injury to the indicated plants):

| Formulation | Percent Injury | | | | | |
| --- | --- | --- | --- | --- | --- | --- |
| | Sorghum, | RPW, | GRFT, | WTG, | BYG, | DAT |
| Flowable propachlor | 0 | 33 | 93 | 85 | 93 | 30 |
| | 0 | 42 | 87 | — | 87 | 78 |
| WP propachlor | 0 | 23 | 85 | 83 | 92 | 30 |
| | 0 | 20 | 87 | — | 87 | 78 |

From the foregoing detailed description it will be apparent to those skilled in the art that the flowable herbicides disclosed and claimed herein provide the art with benefits and advantages not hitherto achieved. As indicated above the primary benefits of the flowable herbicides of this invention relate to the elimination of noxious fumes and dusts, improved bloom and redispersability, while maintaining crop safety and efficacy comparable to analogous herbicide formulations of the prior art. In addition, the flowable herbicides herein provide the convenience and economy of a one-container formulation; i.e., there is no necessity to buy, transport, store, measure and mix the components of two or more containers.

Although this invention has been described with respect to specific modifications, the details thereof are not to be construed as limitations, since it will be apparent that various equivalents and modifications may be resorted to without departing from the spirit and scope of the invention.

We claim:

1. Flowable herbicide having the following composition by weight:
   (a) from 25% to 50% of propachlor herbicide;
   (b) from 0 to 15% of atrazine;
   (c) an emulsifier/suspension system comprising
      (i) hydrated amorphous silicon dioxide: 2–8%
      (ii) polyoxypropylene/polyoxyethylene block copolymer mol. wt. about 6500: 2–8%
      (iii) hydrated aluminum silicate: 0.5–2%
   (d) an inert, low-freezing point polyglycol solvent compatible with components (c) (i)-(iii): 5–15%
   (e) defoamer: 0–0.1%, and
   (f) water: 30–70%
the solid components of said composition having a particle size no greater than about 20 microns.

2. Flowable propachlor herbicide having the following composition by weight:
   (a) propachlor: 40–46%
   (b) an emulsifier/suspension system comprising:
      (i) hydrated amorphous silicon dioxide: 4.0%
      (ii) polyoxypropylene/polyoxyethylene block copolymer, mol. wt. 6500, in aqueous n-butanol: 4.0%
      (iii) kaolin: 1.0%
   (c) ethylene glycol: 8.0%
   (d) silicone defoamer: 0.02%, and
   (e) water: balance,
the solid components of said herbicide being within the range of about 1.0–20 microns.

3. Flowable propachlor/atrazine herbicide having the following composition by weight:
   (a) propachlor: 30–35%
   (b) atrazine: 10–12%
   (c) an emulsifier/suspension system comprising
      (i) hydrated amorphous silicon dioxide: 4.0%
      (ii) polyoxypropylene/polyoxyethylene block copolymer mol. wt. 6500, in aqueous butanol: 4.0%
      (iii) kaolin: 1.0%
   (d) ethylene glycol: 8.0%
   (e) silicone defoamer: 0.02%, and
   (f) water: balance,
the particle size of said herbicide being within the range of from about 1.0–20 microns.

4. Flowable formulations according to any of claims 1, 2 or 3 wherein said solid particle size corresponds to the following distribution:
   95% less than 20 microns
   75% less than 10 microns
   50% less than 5 microns
   25% less than 2.5 microns 5. Flowable formulations according to any of claims 1, 2 or 3 wherein said particle size corresponds to the following distribution:
   95% less than 4.5 microns
   75% less than 2.8 microns
   50% less than 2.4 microns
   25% less than 1.9 microns 6. Process for preparing a flowable herbicide composition having the following composition by weight:
   (a) from 25% to 50% of propachlor;
   (b) from 0 to 15% of atrazine;
   (c) an emulsifier/suspension system comprising:
      (i) hydrated amorphous silicon dioxide: 2–8%
      (ii) polyoxypropylene/polyoxyethylene block copolymer having an average molecular weight of 6500: 2–8%
      (iii) hydrated aluminum silicate: 0.5–2%
   (d) an inert, low-freezing point polyglycol solvent compatible with components (c) (i)-iii: 5–15%
   (e) defoamer: 0–0.1%
   (f) water; which comprises the steps of:
      (1) Adding said emulsifier/suspension system of (c) to said water;
      (3) Blending the mixture of Step 1 until a uniform mixture is obtained;
      (4) Adding the herbicide material described by (a) and (b) to the mixture of Step 3;
      (5) Mixing the mixture of Step 4, at a temperature of about 20°–25° C. until a uniform mixture is produced containing the following particle size distribution:
         95% less than 48 microns
         75% less than 35.5 microns
         50% less than 23 microns
         25% less than 13 microns;
      (6) Feeding the mixture of Step 5 into a wet grinding means, while maintaining the temperature at from about 18°–20° C., and grinding said mixture for a period of time sufficient to produce a solids particle size distribution as follows:
         95% less than 4.5 microns
         75% less than 2.8 microns
         50% less than 2.4 microns
         25% less than 1.9 microns.

* * * * *